United States Patent [19]

Adorante et al.

[11] Patent Number: 5,573,758
[45] Date of Patent: Nov. 12, 1996

[54] METHOD FOR REDUCING INTRAOCULAR PRESSURE IN THE MAMMALIAN EYE BY ADMINISTRATION OF POTASSIUM CHANNEL BLOCKERS

[75] Inventors: Joseph S. Adorante, Irvine; Elizabeth WoldeMussie, Laguna Niguel; Guadalupe Ruiz, Corona, all of Calif.

[73] Assignee: Allergan, Waco, Tex.

[21] Appl. No.: 431,170

[22] Filed: Apr. 28, 1995

[51] Int. Cl.$^6$ ............................................. A61K 31/74
[52] U.S. Cl. ..................... 424/78.04; 514/912; 514/913; 514/914
[58] Field of Search .................. 424/78.04; 514/912, 514/913, 914

[56] References Cited

FOREIGN PATENT DOCUMENTS

89/10757  11/1989  WIPO .
9428900  12/1994  WIPO .

OTHER PUBLICATIONS

Fryklund et al, Acta Physiol Scand: No. 149, 1993, pp. 365–376, The effects of potassium transport inhibitors on intestinal fluid and ion transport in vivo and in vitro.
Camardo et al; *Single–Channel Recording* (Eds: Sakmann, B, Neher, E.); pp. 409–423; Single–Channel Analysis is Aplysia Neurons A Specific K$^+$ Channel Is Modulated by Serotonin and Cyclic AMP.

*Primary Examiner*—Carlos Azpuru
*Attorney, Agent, or Firm*—Robert J. Baran; Martin A. Voet; Howard R. Lambert

[57] ABSTRACT

Pharmaceutical compositions and a method are disclosed for treating glaucoma and/or ocular hypertension in the mammalian eye by administering to the mammalian eye the pharmaceutical composition of the invention which contains, as the active ingredient, one or more compounds having potassium channel blocking activity. Examples of potassium channel blockers utilized in the pharmaceutical composition and method of treatment are quinine, tremogenic indole alkaloids, such as Penitrem A and paspalicine, and insect toxins such as charybdotoxin and iberiotoxin.

10 Claims, 1 Drawing Sheet

METHOD FOR REDUCING INTRAOCULAR PRESSURE IN THE MAMMALIAN EYE BY ADMINISTRATION OF POTASSIUM CHANNEL BLOCKERS

BACKGROUND OF INVENTION

1. Field of the Invention

The present invention is directed to pharmaceutical compositions, and primarily to topically applied ophthalmic compositions comprising as the active ingredient one or more compounds having the ability to block potassium channels in the ciliary epithelium, e.g. to inhibit the transport of potassium ions and fluid secretion in epithelia. The pharmaceutical compositions are useful for reducing intraocular pressure in animals of the mammalian species. In another aspect, the present invention is directed to administering such formulations and compositions to animals of the mammalian species (including humans) for reducing intraocular pressure in the eye.

2. Brief Description of the Art

Glaucoma is an optical neuropathy associated with elevated intraocular pressures which are too high for normal function of the eye, and results in irreversible loss of visual function. It is estimated in medical science that glaucoma afflicts approximately 2 percent of the population over the age of forty years, and is therefore a serious health problem. Ocular hypertension, i.e. the condition of elevated intraocular pressure, which has not yet caused irreversible damage, is believed to represent the earliest phase of glaucoma. Many therapeutic agents have been devised and discovered in the prior art for the treatment or amelioration of glaucoma and of the condition of increased intraocular pressure which precedes glaucoma.

Primary open angle glaucoma (POAG) is associated with a rise in intraocular pressure (IOP). This increase in IOP is believed to contribute to the loss of optic nerve function which ultimately leads to blindness. Reduction of IOP is therefore a crucial component in the management of POAG.

In principle, IOP can be reduced by inhibiting aqueous humor inflow or conversely by stimulating aqueous outflow. Aqueous humor inflow is mediated by ion transport across the ciliary epithelium. The above secretion of aqueous humor produced by the ciliary epithelium is then drained from the eye (aqueous outflow) via the trabecular meshwork into Schlemm's canal.

Because ion transport mediates secretion of aqueous humor, blocking or modulating the relevant ion channels or carriers will consequently inhibit or reduce aqueous formation and thus lower IOP. On the other hand, since the trabecular meshwork (TM) is a major obstacle (resistance pathway) to aqueous outflow, reducing its resistance to the passage of fluid should enhance outflow and lower IOP. Thus, by reducing the volume or size of TM cells it should be possible to enhance outflow by lowering the resistance to the passage of ocular fluid. Cell volume/size is determined by a balance between ion uptake and efflux mechanisms. Therefore, it follows that reducing TM cell volume can be accomplished by either stimulating the ion efflux or inhibiting the ion uptake mechanisms in this cell type.

The drugs currently utilized in the treatment of glaucoma include miotics (e.g., pilocarpine, carbachol, and acetylcholinesterase inhibitors), sympathomimetrics (e.g., epinephrine and dipivalylepinephrine), beta-blockers (e.g., betaxolol, levobunolol and timolol), alpha-2 agonists (e.g., para-amino clonidine) and carbonic anhydrase inhibitors (e.g., acetazolamide, methazolamide and ethoxzolamide). Miotics and sympathomimetics are believed to lower intraocular pressure by increasing the outflow of aqueous humor, while beta-blockers, alpha-2 agonists and carbonic anhydrase inhibitors are believed to lower intraocular pressure by decreasing the formation of aqueous humor. All five types of drugs have potential side effects. Miotics, such as pilocarpine, can cause blurring of vision and other visual side effects which may either decrease patient compliance or require termination of miotic drug therapy. Carbonic anhydrase inhibitors can also cause serious side effects which affect patient compliance and/or necessitate withdrawal of the drug therapy. At least one beta-blocker, timolol, has increasingly become associated with serious pulmonary side effects attributable to its effect on beta-2 receptors in pulmonary tissue.

As a result additional antiglaucoma drugs are being developed, e.g., prostaglandin derivatives, muscarinic antagonists, etc.

In light of the foregoing circumstances, it is clear that a need exists for new, more potent antiglaucoma compositions which avoid or reduce the above-cited side effects and enhance patient compliance, since the foregoing and other anti-glaucoma and ocular hypotensive compounds and agents of the prior art do not provide a treatment or cure for glaucoma and ocular hypertension which is satisfactory in all respects. Therefore, the pharmacological and related arts and sciences continue searching for additional and better anti-glaucoma and ocular hypotensive agents.

Chloride channel blockers such as 5-nitro-2-(3-phenylpropylamino)-benzoate (NPPB) have been shown to inhibit $Cl^-$ transport and fluid secretion/absorption in rat intestine. (See for example, Acta Physiol Scand: No. 149, 1993: pp. 365–376, Fryklund et al., "The effects of potassium transport inhibitors on intestinal fluid and ion transport in vivo and in vitro".)

The use of chloride-channel blockers for reducing the intraocular pressure in the eye of a mammal is disclosed and claimed in U.S. patent application Ser. No. 346,660, which was filed on Nov. 30, 1994 in the names of Adorante et al, which is herein incorporated by reference in its entirety.

In addition, PCT Patent WO 89/10757 discloses the use of potassium channel openers for treating glaucoma.

SUMMARY OF THE INVENTION

Surprisingly it has been discovered in accordance with the present invention that potassium channel blockers are effective as anti-glaucoma agents and as agents for reducing intraocular pressure, when such agents are applied to the mammalian eye in a pharmaceutical composition, preferably in a topical ophthalmic composition. Accordingly, the present invention relates to a method of treating glaucoma, or ocular hypertension by topically administering to the mammalian eye an ophthalmic composition which contains an effective amount of a potassium channel blocker. In particular, to inhibit aqueous humor production (inflow inhibition), the potassium channel that resides at the basolateral membrane of the nonpigmented ciliary epithelial cell (NPE) may be blocked. It is believed that blocking the potassium channel of the NPE cell will inhibit net solute and $H_2O$ efflux and therefore aqueous secretion that will in turn will lower IOP. Some preferred examples of potassium channel blockers are quinine, tremogenic indole alkaloids such as Penitrem A and paspalicine, and insect toxins such as charybdotoxin and iberiotoxin. In particular tremogenic indole alkaloids should be especially potent in blocking the potassium channels of NPE cells since these compounds are highly specific in blocking $Ca^{2+}$-gated Maxi potassium channels: the potassium channel of the NPE cell appears to be a $Ca^{2+}$-gated Maxi potassium channel. Thus, aqueous secretion is inhibited and hence intraocular pressure (IOP) is lowered by blocking potassium channels in the NPE cells.

The ophthalmic compositions of the invention contain the active ingredient in a concentration range of approximately 0.0001 to 0.1 percent weight by volume. The composition itself includes, in addition to the active ingredient, such excipients which are per se well known in the art for preparing ophthalmic compositions, particularly ophthalmic solutions. In accordance with the method of the invention the ophthalmic compositions, preferably ophthalmic solutions are applied topically to the mammalian eye approximately 1 or 2 times daily.

DETAILED DESCRIPTION OF THE INVENTION

Figure 1:
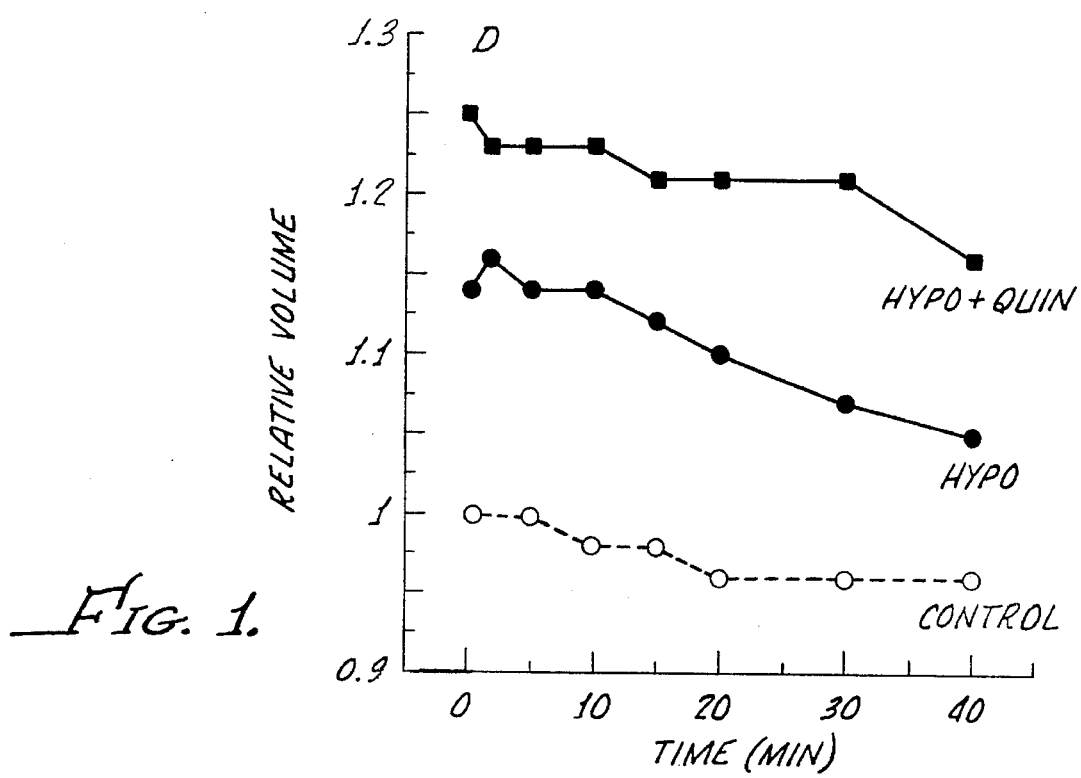
FIG. 1 is a graph showing the effect of the presence of the drug quinine on the regulatory volume decrease (RVD; a readout for net ion and $H_2O$ efflux), on bovine nonpigmented ciliary epithelial (NPE) cells. Inhibition of RVD by quinine is consistent with the notion that $Ca^{2+}$-gated K channels are important in solute and water movement (secretion) in ciliary epithelium.

The compounds which are utilized in accordance with the method of the present invention, and in the pharmaceutical compositions of the present invention, are potassium channel blockers. In this regard the term potassium channel blocker is defined as those compounds or agents which inhibit net potassium flux (current) through a potassium specific pathway (channel, integral membrane protein) within biological membranes. Specific and preferred examples of potassium channel blockers which are utilized in accordance with the present invention are provided.

Pharmaceutically acceptable salts of the potassium channel blockers can also be used in accordance with the present invention. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, such as alkali ions, e.g. sodium, potassium, etc. Organic amine salts may be made with amines, particularly ammonium salts such as mono-, di- and trialkyl amines, e.g. alkyl amines wherein each alkyl group may comprise up to six carbon atoms, or ethanol amines. Salts may also be formed with caffeine, tromethamine and similar molecules. It is only important that the cation of any salt of a potassium channel blocker utilized in the compositions or methods of this invention be able to block potassium channels in the ciliary epithelium.

For reducing intraocular pressure in a mammalian eye, and particularly for treatment of glaucoma in humans suffering from that condition, the active compounds (or mixtures or salts thereof) are administered in accordance with the present invention to the eye admixed with an ophthalmically acceptable carrier. Any suitable, e.g., conventional, ophthalmically acceptable carrier may be employed. A carrier is ophthalmically acceptable if it has substantially no long term or permanent detrimental effect on the eye to which it is administered. Examples of ophthalmically acceptable carriers include water (distilled or deionized water), saline and other aqueous media. In accordance with the invention, the active compounds are preferably soluble in the carrier which is employed for their administration, so that the active compounds are administered to the eye in the form of a solution. Alternatively, a suspension of the active compound or compounds (or salts thereof) in a suitable carrier may also be employed.

In accordance with the invention the active compounds (or mixtures or salts thereof) are administered in an ophthalmically acceptable carrier in sufficient concentration so as to deliver an effective amount of the active compound or compounds to the eye. Preferably, the ophthalmic, therapeutic solutions contain one or more of the active compounds in a concentration range of approximately 0.0001% to approximately 1% (weight by volume) and more preferably approximately 0.0005% to approximately 0.1% (weight by volume).

Any method of administering drugs directly to a mammalian eye may be employed to administer, in accordance with the present invention, the active compound or compounds to the eye to be treated. By the term "administering directly" is meant to exclude those general systemic drug administration modes, e.g., injection directly into the patient's blood vessels, oral administration and the like, which result in the compound or compounds being systemically available. The primary effect on the mammal resulting from the direct administering of the active compound or compounds to the mammal's eye is preferably a reduction in intraocular pressure. More preferably, the active useful compound or compounds are applied topically to the eye or are injected directly into the eye. Particularly useful results are obtained when the compound or compounds are applied topically to the eye in an ophthalmic solution, i.e. as ocular drops.

Topical ophthalmic preparations, for example ocular drops, gels or creams, are preferred because of ease of application, ease of dose delivery and fewer systemic side effects, such as cardiovascular hypotention. An exemplary topical ophthalmic formulation is shown below in Table I. The abbreviation q.s. means a quantity sufficient to effect the result or to make volume.

TABLE I

| Ingredient | Amount (% W/V) |
| --- | --- |
| Active Compound in accordance with the invention, | about 0.0001 to about 1 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |
| Purified Water | as needed to make 100% |

Various preservatives may be used in the ophthalmic preparation described in Table I above. Preferred preservatives include, but are not limited to, benzalkonium potassium, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose and hydroxyethyl cellulose.

Tonicity adjustors may be added as needed or convenient. They include, but are not limited to, salts, particularly sodium potassium, potassium potassium etc., mannitol and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

The ophthalmic solution (ocular drops) may be administered to the mammalian eye as often as necessary to maintain an acceptable level of intraocular pressure in the eye. In other words, the ophthalmic solution (or other formulation) which contains the potassium channel blocker as the active ingredient, is administered to the mammalian eye as often as necessary to maintain the beneficial hypotensive effect of the active ingredient in the eye. Those skilled in the art will recognize that the frequency of administration depends on the precise nature of the active ingredient and its concentration in the ophthalmic formulation. Within these guidelines it is contemplated that the ophthalmic formulation of the present invention will be administered to the mammalian eye approximately once or twice daily.

Specific examples of potassium channel blockers which are used as the active effective ingredients in the ophthalmic compositions of the present invention are described and cited above.

A potassium channel blocker, in accordance with the present invention, may be identified by the method disclosed in Single-Channel Recording, Sakmann et al, published by Plenum Press. (See Chapter 21, by Camardo et al entitled Single-Channel Analysis in Aplysia Neurons A Specific $K^+$ Channel Is Modulated by Serotonin and Cyclic AMP.)

Potassium Channel blockers may also be identified in accordance with the method disclosed below in the Example.

EXAMPLES

The present invention is demonstrated by in vitro and in vivo data. In FIG. 1, 100 µM of quinine were found to depress the regulatory volume decrease (RVD) that occurs following hyposmotic swelling of bovine non-pigmented ciliary epithelial (NPE) cells. In this example, NPE cells were suspended in an isosmotic (295 mOsm) solution containing 100 µM quinine for 30 minutes prior to suspension in a hyposmotoic (198 mOsm) solution. Control cells were subjected to the same hyposmotic solution but without quinine in the medium. Changes in cell volume were measured using a Coulter Counter interfaced to a Coulter Channelyzer. It is noted that, following osmotic swelling, control cells regulate towards their original isosmotic volume while quinine-treated cells remain swollen. The above findings indicate that quinine, via blocking of the potassium channel, inhibits solute and osmotically obliged $H_2O$ efflux.

Because the potassium-dependent ion flux pathways, activated following osmotic cell swelling of NPE cells, are involved in aqueous secretion, quinine will inhibit aqueous humor formation and, thus, lower IOP.

Figure 2:
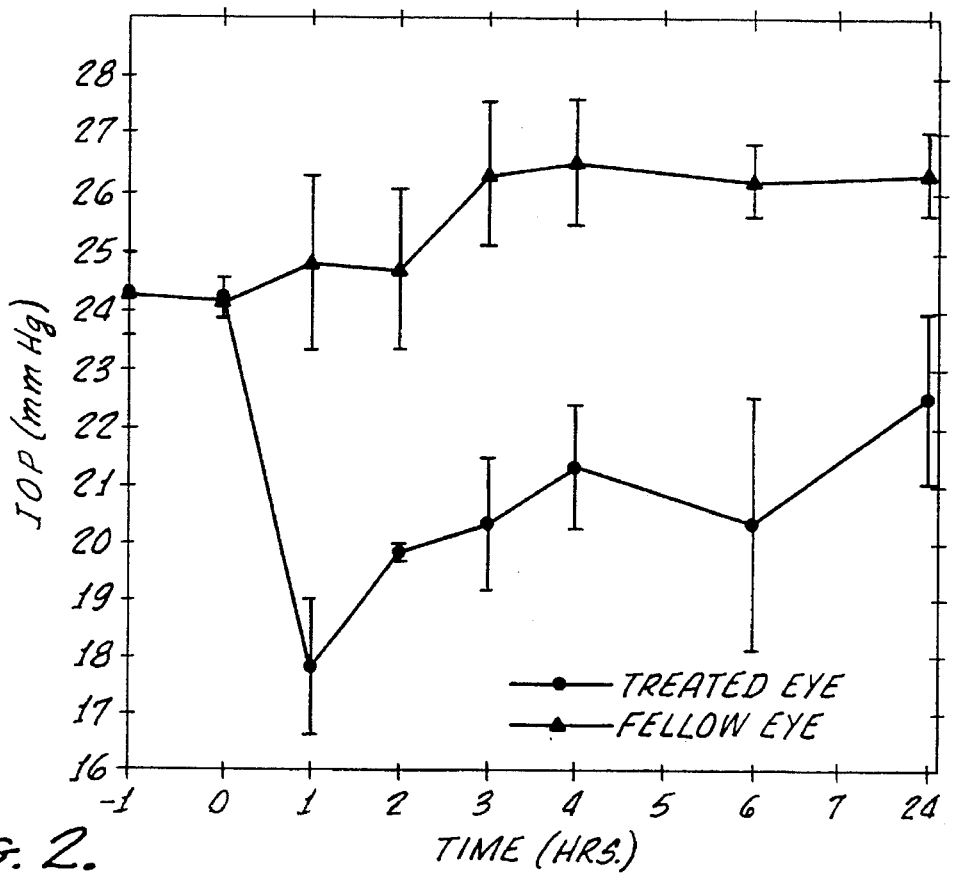
FIG. 2 is a graph showing the effect of intracameral administration of the drug quinine on the intraocular pressure (IOP) in the rabbit eye.

In the in vivo studies normotensive rabbits were injected intracamerally with 1 m M quinine. FIG. 2 shows that 1 m M quinine lowered IOP by 7 mm of Hg and IOP remained depressed for 24 hours. Taken together, the above in vitro and in vivo experiments demonstrate that blocking the potassium channel in the ciliary epithelium will reduce IOP.

One advantage potassium channel inhibition has over other IOP lowering therapies is that the effector, i.e. the ion channel or carrier, is targeted rather than the receptor. Since effector blockage is direct, it should be the most potent and effective way of inhibiting aqueous secretion and hence lowering IOP. On the other hand, targeting a receptor to block an effector is indirect and relies on modulation of a series of cellular events (intracellular messengers/signals) prior to effector inhibition.

In view of the above, it is dear that the scope of the present invention should be interpreted solely on the basis of the following claims, as such claims are read in light of the disclosure.

What is claimed is:

1. A pharmaceutical composition useful for reducing intraocular pressure in the eye of a mammal in need thereof, by blocking $Ca^{2+}$-gated Maxi potassium channels, the composition comprising as its active ingredient a therapeutically effective amount of one or more compounds selected from the group consisting essentially of Penitrem A, paspalicine, charybdotoxin and iberiotoxin.

2. The pharmaceutical composition of claim 1 wherein the compound having potassium channel blocking activity is charybdotoxin.

3. The pharmaceutical composition of claim 1 where the composition is an ophthalmic solution, adapted for administration to the eye of a mammal in the form of eye droplets.

4. The pharmaceutical composition of claim 1 wherein the composition contains approximately 0.0001 to 1 percent weight by volume of said compound having potassium channel blocking activity.

5. A method of treating animals of the mammalian species, including humans, for the purpose of reducing intraocular pressure in the eye of the mammal in need thereof comprising the step of administering to the mammal a pharmaceutical composition which comprises as its active ingredient a therapeutically effective amount of one or more compounds selected from the group consisting essentially of Penitrem A, paspalicine, charybdotoxin and iberiotoxin by blocking $Ca^{2+}$-gated Maxi potassium channels.

6. The method of claim 5 wherein said compound having potassium channel blocking activity is charybdotoxin.

7. The method of treatment of claim 5 wherein the composition is an ophthalmic solution adapted for administration to the eye of a mammal in the form of eye droplets.

8. The method of treatment of claim 5 wherein in the ophthalmic composition the concentration of the compound having potassium channel blocking activity is in the range of approximately 0.0001 to 1 percent weight by volume.

9. The pharmaceutical composition of claim 1 wherein said compound is selected from the group consisting essentially of Penitrem A and paspalicine.

10. The method of claim 5 wherein said compound is selected from the group consisting essentially of Penitrem A and paspalicine.

* * * * *

UNITED STATES PATENT AND TRADEMARK OFFICE
Certificate

Patent No. 5,573,758                                    Patented: November 12, 1996

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Joseph S. Adorante, Elizabeth Woldemussie, Guadalupe Ruiz, Kara Kopper and Alison M. Moore.

Signed and Sealed this Twenty-Fifth Day of May, 1999.

THURMAN K. PAGE
*Supervisory Patent Examiner*
Art Unit 1615